(12) United States Patent
Chi et al.

(10) Patent No.: US 11,844,560 B2
(45) Date of Patent: Dec. 19, 2023

(54) PATH PLANNING DEVICE FOR MULTI-PROBE JOINT CRYOABLATION

(71) Applicant: HYGEA MEDICAL TECHNOLOGY CO., LTD., Beijing (CN)

(72) Inventors: Chen Chi, Beijing (CN); Qianfu Huang, Beijing (CN)

(73) Assignee: HYGEA MEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 18/008,465

(22) PCT Filed: Jun. 2, 2022

(86) PCT No.: PCT/CN2022/096823
§ 371 (c)(1),
(2) Date: Dec. 6, 2022

(65) Prior Publication Data
US 2023/0225779 A1   Jul. 20, 2023

(30) Foreign Application Priority Data

Sep. 7, 2021 (CN) .......................... 202111041282.6

(51) Int. Cl.
*A61B 18/02* (2006.01)
*A61B 34/10* (2016.01)
*A61B 18/00* (2006.01)

(52) U.S. Cl.
CPC .... *A61B 18/02* (2013.01); *A61B 2018/00577* (2013.01); *A61B 2018/0293* (2013.01); *A61B 2034/104* (2016.02); *A61B 2034/107* (2016.02)

(58) Field of Classification Search
CPC .......... A61B 18/02; A61B 2018/00577; A61B 2018/0293; A61B 2034/104; A61B 2034/107
See application file for complete search history.

(56) References Cited

U.S. PATENT DOCUMENTS

2004/0152971 A1* 8/2004 Kukuk ............... A61B 10/0233
                                                              600/424
2009/0221908 A1    9/2009 Glossop
(Continued)

FOREIGN PATENT DOCUMENTS

CN         102598088 A     7/2012
CN         109498155 A     3/2019
(Continued)

OTHER PUBLICATIONS

1st Office Action of counterpart Chinese Patent Application No. 202111041282.6 dated Oct. 20, 2021.
(Continued)

*Primary Examiner* — Daniel W Fowler

(57) ABSTRACT

The disclosure relates to a path planning device for multi-probe joint cryoablation, the device comprising a memory and a processor. The memory stores a computer program, and the processor, when executing the computer program, implements the following steps: acquiring a target region in a medical scanned image of a target object and corresponding to a target tissue to be cryoablated; selecting a single-probe ablation region from the target region; for the single-probe ablation region, obtaining a puncture path of single-probe cryoablation and a corresponding ice ball coverage region; and if the ice ball coverage region does not completely cover target region, then taking the remaining region of the target region from which the ice ball coverage region is excluded as a new target region, and returning to the step of selecting the selecting the single-probe ablation region from the target region.

2 Claims, 2 Drawing Sheets

(56) References Cited

U.S. PATENT DOCUMENTS

| | | | | | |
|---|---|---|---|---|---|
| 2013/0331829 | A1* | 12/2013 | Babkin | .................. | A61B 18/02 |
| | | | | | 606/24 |
| 2014/0201669 | A1* | 7/2014 | Liu | ........................ | A61B 34/10 |
| | | | | | 715/771 |
| 2017/0209218 | A1* | 7/2017 | Sahay | .................... | A61B 6/487 |
| 2018/0360520 | A1* | 12/2018 | Avalle | .................... | A61B 18/02 |
| 2019/0008591 | A1* | 1/2019 | Desai | ..................... | A61B 34/30 |
| 2022/0265359 | A1* | 8/2022 | Isola | ....................... | A61B 18/18 |

FOREIGN PATENT DOCUMENTS

| | | |
|---|---|---|
| CN | 209032618 U | 6/2019 |
| CN | 110151309 A | 8/2019 |
| CN | 111012474 A | 4/2020 |
| CN | 111743626 A | 10/2020 |
| CN | 113116514 A | 7/2021 |
| CN | 113171171 A | 7/2021 |

OTHER PUBLICATIONS

Notice of Allowance of counterpart Chinese Patent Application No. 202111041282.6 dated Nov. 9, 2021.

* cited by examiner

PATH PLANNING DEVICE FOR MULTI-PROBE JOINT CRYOABLATION

CROSS-REFERENCE TO RELATED APPLICATION

The present application claims the priority of Chinese patent application No. 202111041282.6, filed on Sep. 7, 2021 and entitled "Path Planning Device for Multi-probe Joint Cryoablation", which is incorporated herein by reference in its entirety.

FIELD OF THE INVENTION

The present disclosure relates to the technical field of surgical planning, and in particular to a path planning device for multi-probe joint cryoablation.

BACKGROUND OF THE INVENTION

Surgical planning is an emerging medical technical means integrating a digitization technique with medicine, where the digitization technique is used to realize the three-dimensional visualization of a lesion region of a patient, and to help a doctor to complete precise data measurement, preoperative analysis, operation simulation and deduction, and postoperative effect analysis, so as to formulate an operation design solution, which covers preoperative planning, intraoperative navigation and postoperative assessment.

According to the ablation manner, the preoperative planning of a tumor ablation operation can generally be divided into thermal ablation operation planning and cryoablation operation planning. In the thermal ablation preoperative planning, a three-dimensional image of a patient is commonly obtained according to a computed tomography (CT) or magnetic resonance imaging (MRI) medical image of the patient. During the planning of an operation path, a microwave energy field is comprehensively calculated depending on a probe entry point, a probe entry angle, a probe entry depth, ablation probe temperature and an ablation duration of the ablation operation that are inputted, so as to calculate a microwave energy distribution absorbed by a tissue to be ablated per unit volume per unit time, and a temperature field distribution of the tissue to be ablated is calculated by taking the calculated microwave energy field as an internal thermal source. A thermal damage region of the tissue to be ablated is also calculated. Finally, the calculated thermal damage region is displayed on the three-dimensional image of the patient in a fused manner by an image display unit.

In cryoablation, the ablation of a lesion tissue is performed by an ice ball formed at the tail end of an ablation probe, which is different from the thermal ablation manner. In cryoablation, distributions of an energy field and a related temperature field cannot be precisely controlled by means of radio frequency power as in the thermal ablation operation. Therefore, cryoablation requires a different preoperative planning solution than the thermal ablation. For one ablation probe, the shape of the formed ice ball is usually ellipsoidal, the volume thereof is limited, and thus, the ice ball formed by one ablation probe cannot greatly cover a lesion region when it comes to a tumor having a larger volume or an irregular shape. In order to solve the problem of the ablation of a larger lesion, it is usually necessary to conduct a multi-ablation-probe joint operation, i.e., multi-probe joint cryoablation. For the multi-ablation-probe joint ablation, design and planning are required for a puncture point, a puncture path, an ablation time, etc. of each ablation probe. At present, there is a lack of a puncture path planning solution for the multi-probe joint cryoablation.

SUMMARY OF THE INVENTION

The technical problem to be solved by the disclosure is that there is a lack of a puncture path planning solution for multi-probe joint cryoablation.

In order to solve the above problem, the disclosure provides a path planning device for multi-probe joint cryoablation.

Embodiments of the disclosure provide a path planning device for multi-probe joint cryoablation, the device including a memory and a processor. The memory stores a computer program, and the processor, when executing the computer program, implements the following steps: acquiring a target region in a medical scanned image of a target object and corresponding to a target tissue to be cryoablated; selecting a single-probe ablation region from the target region; for the single-probe ablation region, obtaining a puncture path of single-probe cryoablation and a corresponding ice ball coverage region; and if the ice ball coverage region does not completely cover the target region, taking the remaining region of the target region from which the ice ball coverage region is excluded as a new target region, and returning to the step of selecting the selecting a single-probe ablation region from the target region.

BRIEF DESCRIPTION OF THE DRAWINGS

The scope of the disclosure will be further understood from reading the following detailed description of exemplary embodiments in conjunction with the accompanying drawings. The accompanying drawings involved are as follows.

DETAILED DESCRIPTION OF THE EMBODIMENTS

Figure 1:
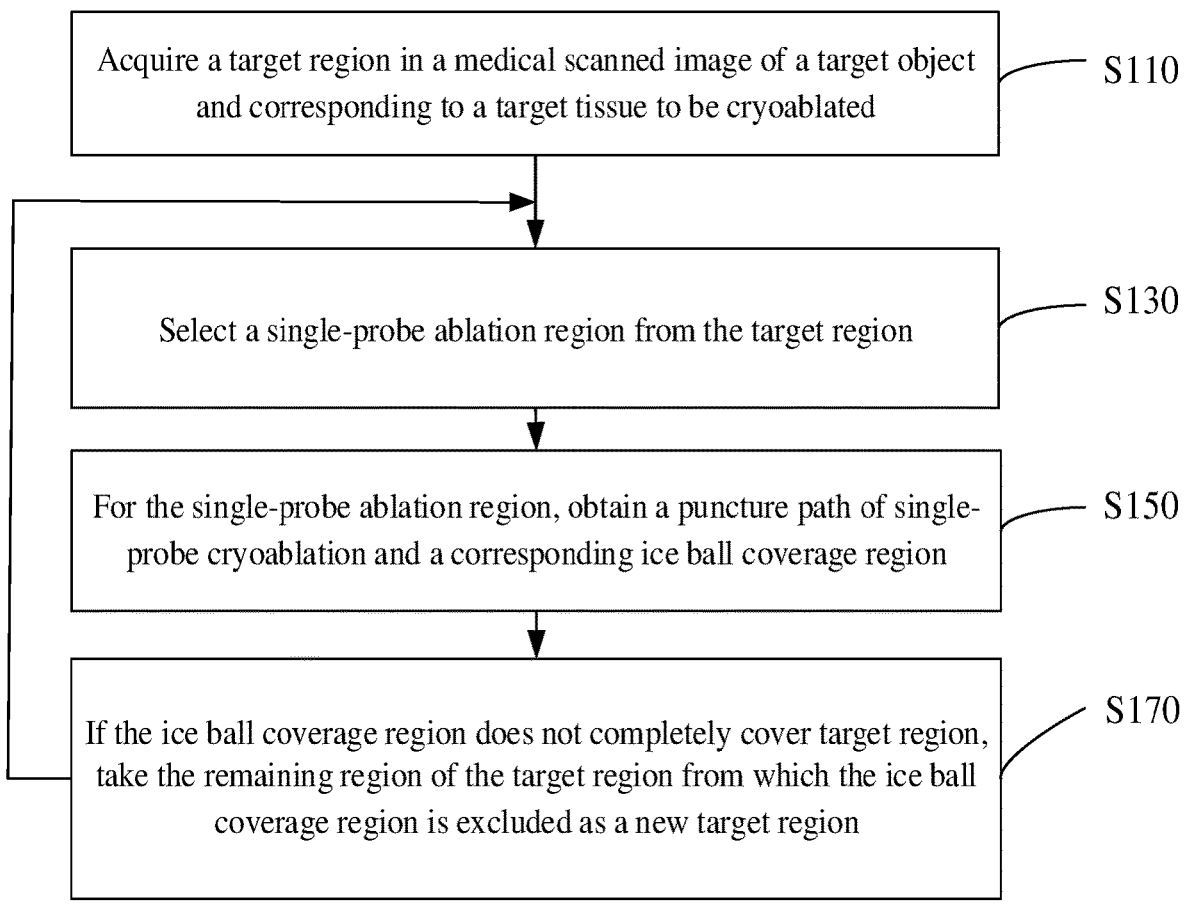
FIG. 1 is a schematic flow diagram of a step implemented by a processor executing a computer program, in a path planning device for multi-probe joint cryoablation in one embodiment.

In order to make the objects, technical solutions and advantages of the disclosure clearer, the implementations of the disclosure will be described in details below in conjunction with the accompanying drawings and embodiments, so as to provide a thorough understanding and practice of an implementation process of how to apply technical means to solve the technical problems and achieve technical effects in the disclosure.

The disclosure mainly relates to the problem of the puncture path planning for multi-probe joint cryoablation operation, and can be applied to the preoperative planning of tumor cryoablation. Previously, the preoperative planning of radiotherapy is quite mature, but the preoperative planning technique of tumor cryoablation poorly develops. An important reason therefor lies in that it is difficult to quickly and precisely predict an ice ball ablation region, which is also a difficult problem that the academic world has always been devoted to solve. Moreover, for the multi-probe joint cryoablation, since a plurality of ablation probes have a plurality of cold sources, the volume of a generated ice ball is greater, such that parameter optimization becomes harder.

Mathematically, the problem of multi-probe joint ablation can be classified into a maximal covering location problem or a P-coverage problem. Such problems focus on how to set P serving stations in order to maximize demand that can be served, under the condition of a known number of serving stations and a known service radius of each serving station. Maximal covering location problem, which is also known as an NP-hard problem (Mark S. Daskin) like some other fundamental problems, was initially put forward by R. L. Church and C. ReVelle, who limit the optimal locating point of a serving station on a network node. They gave the optimal algorithm in a determined key candidate node set in general cases, where a solution is found by means of linear planning, and if the optimal solution is not an integer, the solution is found by using a branch and bound method. Church and Meadows also put forward the pseudo-Hakimi characteristic of the maximal covering location problem, that is, there is an expanded set of finite nodes in any network, and the set at least contains the optimal solution of one maximal covering location problem. Benedict, Hogan, ReVelle and Daskin considered the maximal covering location problem in the case of service system congestion. The probability of any serving station being busy is taken as an exogenous variable, and a target function is to maximize expected demand that can be covered by the serving station. Haldun Aytug and Cem Saydam solved large-scale maximal expected covering location problems by genetic algorithms, including a comparative study. Y. Fernando, et al. compared queueing and non-queueing cases in the maximal expected covering location problem. Berman studied the relationship between the maximal covering location problem and the partial covering location problem. Oded Berman, Dmitry Krass, Oded Berman, Dmitry Krass and Zvi Drezner discussed a maximal covering location problem that is more general than the traditional maximal covering location problem, and give the Lagrange relaxation algorithm. Orhan Karasakal and Esra K. Karasakal discussed the partial covering location problem, defining the degree of coverage. Jorge H. Jaramillo, Joy Bhadury and Rajan Batta introduced an operation strategy of a genetic algorithm for the maximal covering location problem when studying the application of the genetic algorithm in a location problem.

The multi-probe joint ablation problem can be equivalent to the maximal covering location problem of a three-dimensional space. However, no direct solution has been found so far. In order to solve this problem, the disclosure provides a path planning device for multi-probe joint cryoablation.

In one embodiment, the path planning device for multi-probe joint cryoablation includes a memory and a processor. The memory stores a computer program, and as shown in FIG. 1, the processor, when executing the computer program, implements the following steps S110 to S140.

At S110, a target region in a medical scanned image of a target object and corresponding to a target tissue to be cryoablated is acquired.

The target object refers to an object needing a cryoablation operation. The medical scanned image of the target object is an image obtained by performing scanning examination on the target object, such as a CT image and an MRI image. The target tissue refers to a body tissue needing cryoablation, such as a diseased organ. The target region is a region in the target tissue where a lesion is located. Taking a liver tumor as an example, the target tissue to be cryoablated is a liver, and the target region is a tumor lesion region of the liver. For example, the target region can be obtained by processing the medical scanned image.

At S120, a single-probe ablation region is selected from target region.

The single-probe ablation region is a partial region in the target region. For example, a partial region can be randomly selected from the target region and taken as the single-probe ablation region at this time.

At S130, for the single-probe ablation region, a puncture path of single-probe cryoablation and a corresponding ice ball coverage region are obtained.

The single-probe cryoablation refers to cryoablation performed by using one ablation probe. For example, the obtained puncture path is a puncture path required for performing single-probe cryoablation on the current single-probe ablation region, and the corresponding ice ball coverage region is a coverage region, on the puncture path, of the ice ball formed at the tail end of an ablation probe.

At S140, if the ice ball coverage region does not completely cover target region, then the remaining region of the target region from which the ice ball coverage region is excluded is taken as a new target region.

If the ice ball coverage region does not completely cover the target region, then the new target region is selected. After the new target region is obtained, step S120 is returned. The selection of the single-probe ablation region and the acquisition of the puncture path are recurrently performed for multiple times in this way, until the currently obtained ice ball coverage region completely covers the current target region. The puncture path of the single-probe ablation region that is obtained each time is the puncture path of each probe that is required for performing multi-probe joint cryoablation on the target tissue of the target object.

The path planning device for multi-probe joint cryoablation repeatedly selects a single-probe ablation region from an updated target region to obtain a puncture path and an ice ball coverage region of the single-probe ablation region, removes the previous ice ball coverage region from the target region when the ice ball coverage region does not completely cover the target region, so as to update the target region, and repeatedly executes same until the current ice ball coverage region completely covers the current target region, which represents that overall path planning has been completed. The puncture path of the single-probe ablation region that is obtained each time is the puncture path of each probe that is required for performing multi-probe joint cryoablation on a target tissue of a target object. In this way, multi-probe puncture paths for performing multi-probe joint cryoablation on a target tissue to be cryoablated can be accurately obtained, thereby realizing the puncture path planning of each probe in the multi-probe joint cryoablation.

The path planning device for multi-probe joint cryoablation can be suitable for solving a tumor region having a larger volume and an irregular shape through multi-probe joint ablation, and can also solve a plurality of dispersed small tumor regions. By applying the path planning device for multi-probe joint cryoablation, it is possible to assist in finding multi-probe puncture paths, such that the multi-probe puncture paths cause less damage to normal tissues as much as possible, while achieving a tumor ablation effect.

In one of the embodiments, step S110 includes step (a1) to step (a2).

At step (a1), a medical scanned image of a target object is acquired, and an image of a target tissue to be cryoablated is extracted from the medical scanned image.

For example, this step may be performed by receiving a medical scanned image generated by a scanning device scanning the target object. For example, it may be performed by extracting an image of the target object by performing quick and automatic three-dimensional image segmentation on the medical scanned image by using a neural network deep learning method. For example, quick and automatic three-dimensional image segmentation is performed based on a CT sequential scanned image of a liver tumor, by using the neural network deep learning method, so as to extract three-dimensional structures of the liver tumor, a liver and a key anatomical structure, and other human body anatomical structures.

At step (a2), an edge contour of a lesion is outlined in the image of the target tissue, so as to obtain a target region corresponding to the target tissue.

For example, this step may be performed by receiving a marking instruction of a user, and marking the edge contour in the image of the target tissue in response to the marking instruction, so as to outline the edge contour. For example, the user marks the contour of the tumor in the image of the target tissue by using an input apparatus such as a mouse.

As mentioned above, the medical scanned image of the target object is acquired, the image of the target tissue is extracted from the medical scanned image, and the target region is obtained from the image of the target tissue, where extraction is performed step by step from a large range to a small range, such that a lesion region needing cryoablation can be accurately obtained.

For example, step S120 can involve receiving a region selection instruction input by the user, and selecting a region designated by the selection instruction from the target region, so as to obtain the single-probe ablation region. It can be understood that the single-probe ablation region can also be selected from the target region by using another method. For example, the single-probe ablation region is selected from the target region on the basis of the target region and according to a preset selection direction and a preset selection size.

Due to the actually physical thermodynamics effect, an ablation region of a plurality of ice balls is greater than the sum of ablation regions of all the single ice balls. Therefore, approximation simplification is performed, that is, it is considered that the ablation region of the plurality of ice balls is equal to a union set of the separate ablation regions of all the ice balls. Each time step S120 is recurrently executed, one region is randomly selected from the currently corresponding target region as the current single-probe ablation region, so that the ice balls can cover the tumor part as much as possible, so as to reduce damage to normal tissues as much as possible. For example, after the target region corresponding to the target tissue to be cryoablated is acquired, step S120 is executed for the first time, where the current target region is an overall lesion region needing cryoablation. After step S140 is executed, step S120 is executed for the second time, where the new target region is a remaining lesion region of the original overall lesion region from which the ice ball coverage region obtained for the first time is excluded.

In one of the embodiments, step S130 includes step (b1) and step (b2).

At step (b1), a puncture point center of the single-probe ablation region is acquired.

At step (b2), a puncture path for performing single-probe cryoablation on the single-probe ablation region, and a corresponding ice ball coverage region are obtained depending on the puncture point center.

The puncture point center is acquired first, and the puncture path of the single-probe ablation region and the corresponding ice ball coverage region are then obtained on the basis of the puncture point center, such that the accuracy is high. For example, step (b2) may be performed by using a known calculation method for acquiring a single-probe puncture path and an ice ball coverage region. For example, by using an existing tumor puncture path obtaining method, the volume of the ice ball coverage region and the ratio of the ice ball coverage region to the lesion region can be calculated and analyzed, a reference time for complete coverage is given, the volume of a non-lesion region that is covered by an ice ball is analyzed, and finally, the optimal puncture path is given by integrating various indexes.

In one of the embodiments, step (b1) includes: selecting a plurality of non-coplanar points from the edge of the single-probe ablation region to obtain circumscribed points; and determining a homocentric sphere of the plurality of circumscribed points, and taking the center of the homocentric sphere as the puncture point center of the single-probe ablation region.

For example, the homocentric sphere may be a circumscribed sphere of the single-probe ablation region, the single-probe ablation region is within the circumscribed sphere of N points, and the volume of the circumscribed sphere is smaller than the volume of an ice ball of a single probe. At this time, the lesion volume within the circumscribed sphere is an ablation region currently needing to be solved by using single-probe cryoablation. The circumscribed points are selected, the homocentric sphere is determined, and the center of the homocentric sphere is taken as the puncture point center, such that the obtained puncture point center is accurate and reliable, thereby indirectly improving the accuracy and reliability of the puncture path.

In one of the embodiments, after step S130, the method further includes: counting a current ablation probe quantity.

The current ablation probe quantity is a total required ablation probe quantity until the puncture path and the ice ball coverage region are obtained this time. For example, one single-probe ablation region corresponds to one instance of single-probe cryoablation, and one instance of single-probe cryoablation corresponds to one puncture path, one ice ball coverage region and the use of one ablation probe. Therefore, the current ablation probe quantity is equal to the total number of currently obtained puncture paths, and is equal to the number of single-probe ablation regions that are selected as of now. For example, as of now, step S120 and step S130 are executed four times in total, the single-probe ablation region is selected four times, four puncture paths are obtained, and thus the current ablation probe quantity is four. For example, the ablation probe quantity can be initialized to one after step S120 and before step S130, and after the next execution of step S110, a new ablation probe quantity is obtained on the basis of the original ablation probe quantity plus one. The current total ablation probe quantity is counted, so as to facilitate recording a probe quantity required for multi-probe joint cryoablation, thereby facilitating a user's reference and usage.

For example, in one of the embodiments, after step S130, the method further includes: if the ice ball coverage region completely covers the target region, then determining whether the ablation probe quantity is less than or equal to a preset value; if so, then recording all the obtained puncture paths of single-probe cryoablation and a total ablation probe quantity; or if not, then taking the target region corresponding to the target tissue to be cryoablated as the current target region again, and re-executing step S120.

The preset value is the number of probes limited to be used, and can be set according to an actual situation. For example, the present value can be set depending on the number of ablation probes limited to be used by an operation machine. It the ice ball coverage region covers the current target region, then it indicates that there is no remaining region needing to be processed, and so far, all the puncture paths of the target region corresponding to the target tissue are obtained, and overall path planning is completed. At this time, determination and analysis are performed on the current total ablation probe quantity; and if it does not exceed the preset value, then it indicates that the number of ablation probe planned to be used is within an allowable range, or if the current total ablation probe quantity exceeds the preset value, then it indicates that the number of ablation probes planned to be used exceeds limitation, and reset is performed to re-select a single-probe ablation region from the target region corresponding to the target tissue to be cryoablated, so as to re-plan a puncture path. In this way, it can be ensured that the planned ablation probe quantity meets a limitation requirement. It should be understood that, in another embodiment, when the ablation probe quantity is less than or equal to the preset value, it is also possible to record another piece of information, for example, the puncture point center of single-probe cryoablation, so as to record the position of the ice ball.

In one of the embodiments, after all the obtained puncture paths of single-probe cryoablation and a total ablation probe quantity are recorded, the method further includes: generating a path planning solution of multi-probe joint cryoablation depending on all the obtained puncture paths of single-probe cryoablation and a total ablation probe quantity.

All the obtained puncture paths of single-probe cryoablation include puncture paths obtained every time step S130 is executed as of now. The total ablation probe quantity is the current ablation probe quantity as of now, and is equal to the quantity of all the obtained puncture paths. For example, the path planning solution is information including all the puncture paths and the total ablation probe quantity, for notifying a user of the puncture paths and the ablation probe quantity required for performing multi-probe joint cryoablation on the target tissue, which will facilitate the user's reference so as to improve the operation precision.

In each path planning solution, at the beginning, a partial region is randomly selected from a target region as a single-probe ablation region for puncturing this time, and therefore there may be a plurality of path planning solutions with the first selected puncture position varying. For example, each time a path planning solution of multi-probe joint cryoablation is obtained, execution is performed again from step S120, selecting another initial region from the target region as an initial single-probe ablation region, and execution is recurrently performed until another path planning solution of multi-probe joint cryoablation is obtained.

For example, after the path planning solution of multi-probe joint cryoablation is generated depending on all the obtained puncture paths of single-probe cryoablation and the total ablation probe quantity, the method further includes: calculating a value degree for each path planning solution; and selecting and outputting a path planning solution having the highest value degree as an optimal path planning solution.

The value degree represents a criteria for evaluating a path planning solution. For example, the higher the value degree, the greater the ablation effect. The value degrees of a plurality of path planning solutions are analyzed, and an optimal path planning solution is selected, thereby improving the effect of path planning.

The design idea of multi-probe joint cryoablation is based on the following target 1 and target 2.

Target 1: a tumor ablation region is maximized; and
target 2: the damage to health tissues is minimized.

For example, calculating a value degree for each path planning solution includes:

$$r_n = \frac{\alpha \cdot V_{a_n}}{V_A - \beta V_{b_n}}.$$

where $a_n = \cup (A \cap P_i^n)$ $b_n = \cup P_i^n - a_n$ where $r_n$ is the value degree for an nth path planning solution; $\alpha$ is a first preset weight, $\beta$ is a second preset weight, $a_n$ is an ablated region of a target tissue, $b_n$ is a damaged region of a health tissue, $V_{a_n}$ is the volume of the ablated region of the target tissue, $V_{b_n}$ is the volume of the damaged region of the health tissue, A is a target region, $V_A$ is the volume of the target region, and $P_i^n$ is an ice ball coverage region of an ith single-probe ablation of the nth path planning solution.

For example, $a_n$ represents a region set of ice ball coverage regions (ice ball size) of single-probe cryoablation that are located within the target region (a lesion region) in the nth path planning solution, i.e. a lesion tissue ablated region. $b_n$ represents the set of the ice ball coverage regions of single-probe cryoablation in the nth path planning solution, from which the lesion tissue ablated region $a_n$ is excluded. The greater the value of $r_n$, the more thoroughly ablation is performed, and the less the damage to the health tissue. In general cases, $V_{a_n}/V_{b_n}=1$ is expected, that is, a tumor region is completely ablated, and the value of $r_n$ is greater as much as possible. The following equation is used:

$$r_n = \frac{\alpha \cdot V_{a_n}}{V_A - \beta V_{b_n}}.$$

A value degree is calculated, where both the degree of ablation and the degree of damage to a health tissue are taken into consideration, such that whether the path planning solution is good or not can be accurately reflected.

Figure 2:
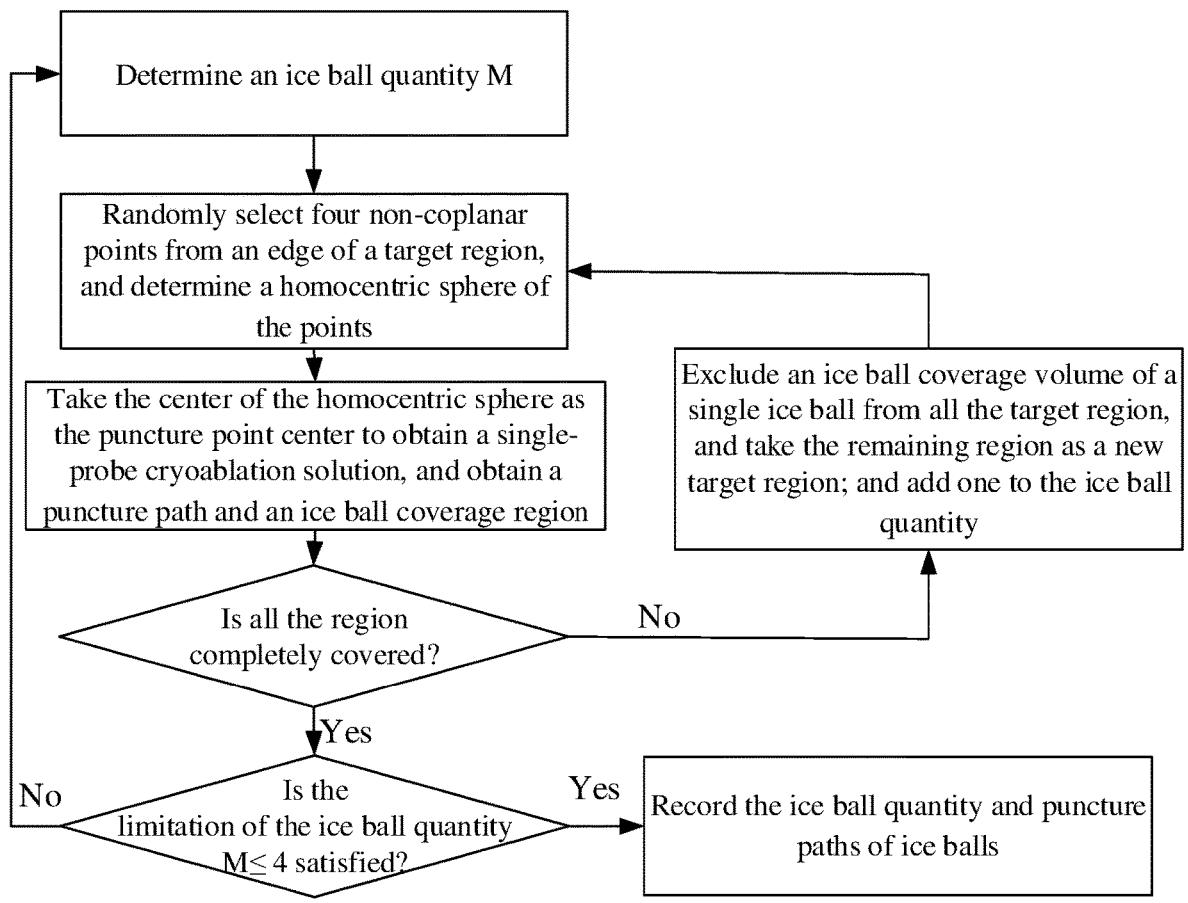
FIG. 2 is a schematic partial flow diagram of a step implemented by a processor executing a computer program, in a path planning device for multi-probe joint cryoablation in another embodiment.

In an exemplary embodiment, the processing flow after step S110 is as shown in FIG. 2. An ablation region is calculated by using a random greedy algorithm, and the steps are as follows:

1. setting an initial ice ball quantity (an ablation probe quantity) M=1;
2. Randomly selecting four non-coplanar points from the edge of a target region, and determining a homocentric sphere of them;
3. taking the center of the homocentric sphere as a puncture point center, obtaining an ablation solution of single-probe cryoablation, and obtaining a puncture path and an ice ball coverage region;
4. excluding an ice ball coverage volume of a single ice ball from all the target region, and the remaining region serving as a new target region;
5. adding one to the ice ball quantity, and repeating steps 2 to 5 until the initial overall target region is completely covered by the ice balls; and
6. determining whether the quantity of ice balls covering all the regions exceeds a limitation of a machine, where the maximum ice ball quantity of a Kangbo knife being limited to four is taken as an example; if the limitation is exceeded, then returning to the first step, re-starting the selection of an initial value; or if the limitation is not exceeded, then recording the current ice ball quantity and puncture paths of ice balls.

The technical features of the embodiments can be combined in any manner. In order to provide a concise description, all possible combinations of all the technical features of the embodiments may not be described; however, these combinations of the technical features should be construed as disclosed in the description as long as no contradiction occurs.

By utilizing the implementations provided in the disclosure, a single-probe ablation region is repeatedly selected from an updated target region to obtain a puncture path and an ice ball coverage region of the single-probe ablation region, the previous ice ball coverage region is removed from the target region when the ice ball coverage region does not completely cover the target region, so as to update the target region, and same is repeatedly executed until the current ice ball coverage region completely covers the current target region, which represents that overall path planning has been completed. The puncture path of the single-probe ablation region that is obtained each time is the puncture path of each probe that is required for performing multi-probe joint cryoablation on a target tissue of a target object. In this way, multi-probe puncture paths for performing multi-probe joint cryoablation on a target tissue to be cryoablated can be accurately obtained, thereby realizing the puncture path planning of each probe in the multi-probe joint cryoablation. On this basis, the value degree for each multi-probe joint path planning solution is calculated, and the optimal multi-probe joint path planning solution is obtained through comparison, so as to help an operator to precisely plan an operation solution.

The implementations disclosed in the disclosure are as stated above, but the content is only implementations used for facilitating the understanding of the disclosure, rather than being used for limiting the disclosure. Any of those skilled in the technical field to which the disclosure belongs can make any modification and change to the form and details of the implementation without departing from the spirit and scope of the disclosure, but the scope of protection of the disclosure shall be defined in the appended claims.

The invention claimed is:

1. A path planning device for multi-probe joint cryoablation, comprising a memory and a processor, wherein the memory stores a computer program, and the processor, when executing the computer program, implements the following steps:
acquiring a target region in a medical scanned image of a target object and corresponding to a target tissue to be cryoablated, wherein the target region is a region in the target tissue where a lesion is to be located;
randomly selecting a partial region obtained from the target region acquired in the acquiring step as a current single-probe ablation region;
obtaining, for the current single-probe ablation region selected in the randomly selecting step, a puncture path of a current ablation probe and a corresponding ice ball coverage region, wherein the corresponding ice ball coverage region is a coverage region, on the puncture path, of an ice ball to be formed at a distal end of the current ablation probe;
counting a current ablation probe quantity, wherein the current ablation probe quantity is equal to a total number of currently obtained puncture paths;
if the corresponding ice ball coverage region does not completely cover the target region acquired in the acquiring step, then determining whether the current ablation probe quantity exceeds a preset value, wherein the preset value is a maximum number of probes to be used;
if the current ablation probe quantity does not exceed the preset value, then taking a remaining region of the target region from which the ice ball coverage region is excluded as a new target region, returning to the randomly selecting step and adding one to the current ablation probe quantity; or
if the current ablation probe quantity exceeds the preset value, then returning to the randomly selecting step;
if the corresponding ice ball coverage region completely covers the target region, then determining whether the current ablation probe quantity is less than or equal to the preset value;
if the current ablation probe quantity is less than or equal to the preset value, then recording all the obtained puncture paths of the ablation probes and a total ablation probe quantity, wherein all the obtained puncture paths of the ablation probes include puncture paths obtained every time the step of obtaining the puncture path of the ablation probe was performed, and the total ablation probe quantity is a total number of ablation probes necessary to produce an ice ball coverage region that completely covers the target region;
generating a path planning solution of multi-probe joint cryoablation depending on all the obtained puncture paths of the current ablation probes and the total ablation probe quantity, for notifying a user of the puncture paths and the ablation probe quantity required for performing multi-probe joint cryoablation on the target tissue; or
if the current ablation probe quantity is not less than or equal to the preset value, then taking the target region corresponding to the target tissue to be cryoablated as the current target region again, and re-executing the randomly selecting step,
wherein each time the path planning solution of multi-probe joint cryoablation is obtained, the steps are executed again from the randomly selecting step to obtain a plurality of the path planning solutions of multi-probe joint cryoablation, and
after the step of obtaining the plurality of the path planning solutions of multi-probe joint cryoablation, the steps further comprise:
calculating a value degree for each path planning solution; and
selecting and outputting the path planning solution having a highest value degree as an optimal path planning solution,
wherein calculating the value degree for each path planning solution is based on the following target 1 and target 2:
target 1: a tumor ablation region $a_n$ maximized; and
target 2: damage to healthy tissues $b_n$ is minimized;
the step of calculating the value degree for each path planning solution comprises:

$$r_n = \frac{\alpha \cdot V_{a_n}}{V_A - \beta V_{b_n}}.$$

wherein $$a_n = \cup (A \cap P_i^n)$$

$$b_n = \cup P_i^n - a_n$$

where $r_n$ is the value degree for an $n^{th}$ path planning solution; $\alpha$ is a first preset weight, $\beta$ is a second preset weight, $a_n$ is an ablated region of a target tissue, and $a_n$ represents a region set of ice ball coverage regions of single-probe cryoablation that are located within the target region in the $n^{th}$ path planning solution, wherein the target tissue is a body tissue needing cryoablation; $b_n$ is a damaged region of a healthy tissue, and $b_n$ represents the set of the ice ball coverage regions of single-probe cryoablation in the $n^{th}$ path planning solution, from which a lesion tissue ablated region $a_n$ is excluded, wherein the healthy tissue is other tissues in the body tissue except the target tissue; $V_{a_n}$ is a volume of the ablated region of the target tissue $a_n$, $V_{b_n}$ is a volume of the damaged region of the healthy tissue $b_n$, A is a target region, $V_A$ is a volume of the target region A, and $P_i^n$ is the ice ball coverage region of an $i^{th}$ single-probe cryoablation of the $n^{th}$ path planning solution.

2. The path planning device for multi-probe joint cryoablation according to claim 1, wherein the step of acquiring the target region in the medical scanned image of the target object and corresponding to the target tissue to be cryoablated comprises:

acquiring a medical scanned image of a target object, and extracting an image of a target tissue to be cryoablated from the medical scanned image; and outlining an edge contour of a lesion in the image of the target tissue, so as to obtain a target region corresponding to the target tissue.

* * * * *